United States Patent [19]
Umezawa et al.

[11] 3,975,366
[45] Aug. 17, 1976

[54] PROCESS FOR THE PRODUCTION OF NEW PEPSTATINS HAVING ANTI-PEPSIN ACTIVITY

[75] Inventors: Hamao Umezawa, Tokyo; Tetsuji Miyano, Nagoya; Kohtaro Funaishi, Okazaki; Tomio Takeuchi, Tokyo; Takaaki Aoyagi, Fujisawa, all of Japan

[73] Assignee: Zaidan Hojin Biseibutsu Kagaku Kenkyu Kai, Tokyo, Japan

[22] Filed: Feb. 4, 1975

[21] Appl. No.: 547,083

Related U.S. Application Data

[60] Division of Ser. No. 387,139, Aug. 9, 1973, Pat. No. 3,869,347, which is a continuation-in-part of Ser. No. 233,533, March 10, 1972, abandoned.

[30] Foreign Application Priority Data

Mar. 26, 1971 Japan.............................. 46-17292

[52] U.S. Cl............................ 260/112.5 R; 424/94; 424/177

[51] Int. Cl.²................ C07C 103/52; C08H 1/00
[58] Field of Search........................... 195/80 R, 65; 260/112.5 R; 424/94, 177

[56] References Cited
UNITED STATES PATENTS

| | | |
|---|---|---|
| 3,819,486 | 5/1974 | Murao et al. ............... 260/112.5 R |
| 3,840,516 | 10/1974 | Umezawa et al............. 260/112.5 R |
| 3,869,347 | 3/1975 | Umezawa et al.................. 195/80 R |

*Primary Examiner*—Lewis Gotts
*Assistant Examiner*—Reginald J. Suyat
*Attorney, Agent, or Firm*—Brady, O'Boyle & Gates

[57] ABSTRACT

A process for producing new pepstatins having anti-pepsin activity by cultivating a pepstatin producing strain in a nutrient medium containing assimilable carbon sources and nitrogen sources, and extracting the new pepstatins from the cultivated broth or medium.

1 Claim, 2 Drawing Figures

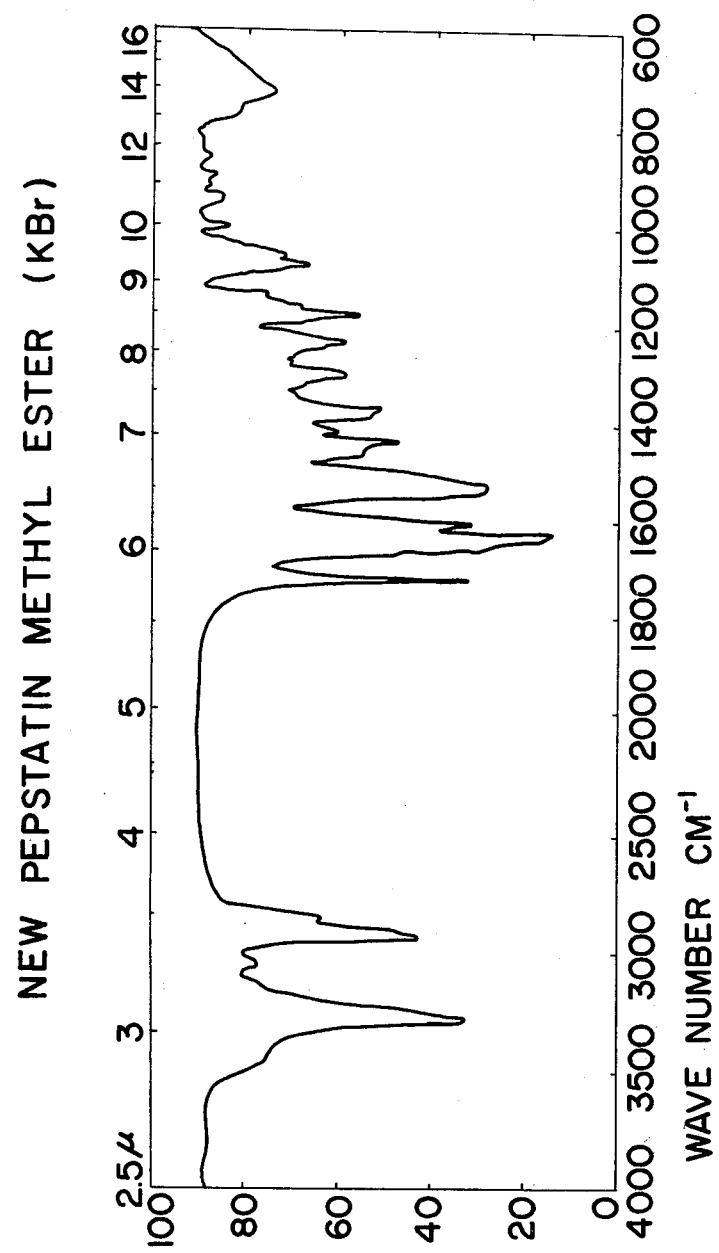

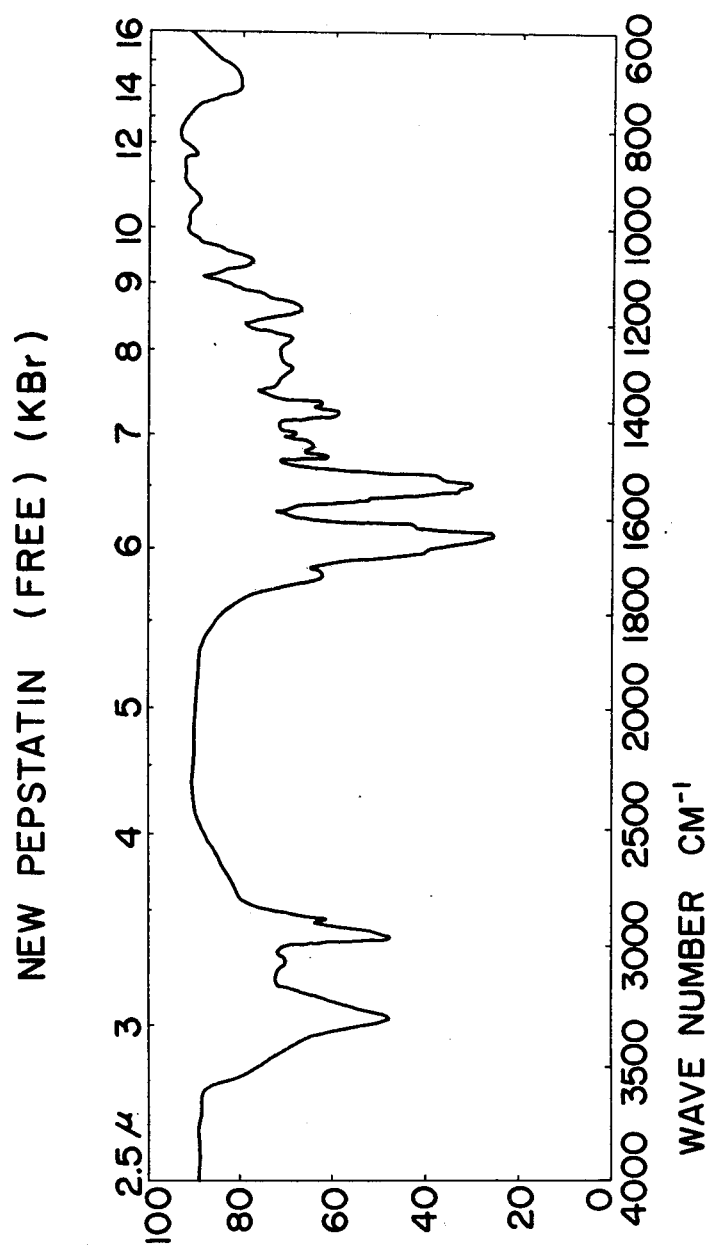

PROCESS FOR THE PRODUCTION OF NEW PEPSTATINS HAVING ANTI-PEPSIN ACTIVITY

CROSS-REFERENCE TO RELATED APPLICATION

This is a division of application Ser. No. 387,139, filed Aug. 9, 1973, now U.S. Pat. No. 3,869,347, which is a continuation-in-part of our copending application Ser. No. 233,533, filed Mar. 10, 1972, now abandoned.

This invention relates to processes for the production of new pepstatin group substances produced by pepstatin producing microorganisms. Umezawa, one of the said inventors, and his co-workers discovered pepstatin as an agent effective against stomach ulcer. Its producing microorganisms are identified as *Streptomyces testaceus* (ATCC No. 21469) Hamada et Okami and *Streptomyces argenteolus var. toyonakensis*. (ATCC No. 21468). Pepstatin is a pentapeptide containing N-acylated isovaleric acid at N-terminal and free carboxylic acid at C-terminal. (J. Antibiotics, 23, 259–262, 1970, ibid., 23, 263–265, 1970). Pepstatin can be obtained by cultivating a pepstatin-producing strain in a nutrient medium containing peptone or other nitrogen source, and extracting from its cultivated broth to purify. Pepstatin can be obtained also as its metal-salts, amides or esters, as described in the Japanese Patent Application No. 46166/69 by Umezawa et al. and corresponding U.S. application Ser. No. 37,165, Filed May 4, 1970, now U.S. Pat. No. 3,740,319. The inventors studied pepsin, inhibitors in the cultured broth of the above pepstatin producing strains under various conditions and found more than two additional pepstatin-like substances which have anti-pepsin activity as pepstatin but differ from pepstatin on silica gel thin layer chromatography and in the amide forming fatty acid moiety of pepstatin on gas chromatography of the acid hydrolysates.

One of the new pepstatins, called pepstatin B, can be crystallized as fine needle form of its methyl ester from methanol solution. It melts at about 254°–255°C and elementary analysis gives C, 60.4%; N, 9.74%; H, 9.38%; calculated to be $C_{36}H_{67}N_5O_9$ (C, 60.6%; H, 9.40%; N, 9.82%). Optical rotation is $[a]_D^{20} = -95.5°$ (C=0.5, acetic acid). It gives a blue color by Rydon-Smith reaction as pepstatin and red color by hydroxylamine-ferric chloride reaction. The methyl ester of pepstatin B is moderately soluble in dimethylformamide, dimethylsulfoxide and acetic acid, but hardly soluble in water, chloroform, benzene, ethyl acetate and ether. It is more soluble in methanol than pepstatin methyl ester (5–10 mg/cc).

The acid hydrolysate of pepstatin B methyl ester by 20% HCl for 16 hours at 105°C was extracted with ether and applied to gas chromatography and two dimentional thin layer chromatography. From ether extract, n-caproic acid was found. From the aqueous layer, valine and alanine (2:1) were found in addition to 3-hydroxy-4-amino-6-methylheptanoic acid. Therefore, the structure of pepstatin B was calculated to be the n-caproic acid amide analog of pepstatin having the structural formula:

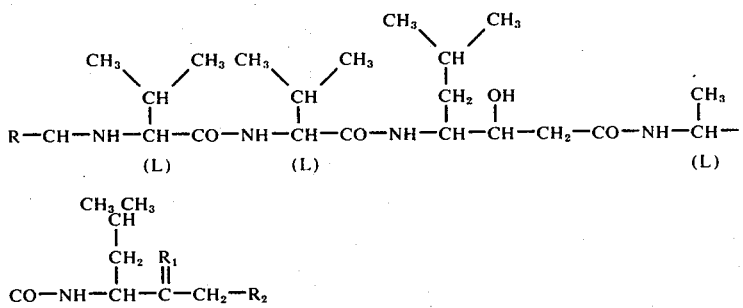

Wherein R is the n-coproyl group, $R_1$ is

and $R_2$ is COOH.

On silica gel thin layer chromatography with the solvent system (chloroform : methanol : acetic acid = 95:4:1), the Rydon-Smith color reaction of pepstatin B methyl ester gave Rf value of 0.39 and pepstatin methyl ester gave 0.35. The anti-pepsin activity of pepstatin B methyl ester showed the same as that of pepstatin methyl ester.

Thus we have discovered that pepstatin producing strains can produce pepstatin-like compounds wherein the fatty acid moiety is substituted by n-caproic acid. The inventors also confirmed the pressure of another pepstatin-like compound called pepstatin C containing isocaproic acid at the amide forming moiety and its methyl ester showed the same Rf value as pepstatin B (0.39). Its structural formula is as above wherein R is the isocaproyl groups $R_1$ is

and $R_2$ is COOH. A third pepstatin-like compound whose methyl ester shows Rf 0.42 has also been found. This anti-pepsin principle was obtained as crystals of fine needle form and its acid hydrolysate gave the same amino acids and 5 fatty acids of $C_5$—$C_{16}$ on gas chromatographic analysis.

The new pepstatins of this invention can be defined as pepstatins containing $C_5$–$C_{16}$ fatty acids, such as n-caproic acid or isocaproic acid different from isovaleric acid.

According to this invention, new pepstatins can be obtained by the following procedures: Pepstatin producing strain is inoculated in a nutrient medium containing casein, skimmed milk and/or soybean meal as nitrogen source, and incubated for 3–10 days under ordinary aerobic condition until anti-pepsin activity of the broth reaches maximum. The active principle can be extracted with n-butanol from cultured broth or its filtrate or with methanol from mycelical mass. The extract thus obtained is concentrated to syrup or to yellow precipitates. The Syrup is put into 5–20 volumes of water by drop-seise to form a precipitate and the precipitate is filtered. The precipitate is dried to a crude state of the new pepstatins. The crude pepstatin is dissolved in lower alcohols and esterified by heating or standing for several hours at room temperature or higher temperature with a small amount of esterifying catalysts such as hydrochloric acid, sulfuric acid, paratoluene sulfonic acid, thionylchloride, phosphorouspentachloride, or phosphorousoxytrichloride, etc. The methyl ester of the crude new pepstatins resulted from methylesterifying is a mixture and the major part of the pepstatin methyl ester can be crystalized from methanol solution. When this crystalline fraction was examined on thin layer chromatography, the methyl ester of original pepstatin and the new pepstatins were found at the rate of 1:1. And the latter was concentrated in mother liquid and can be concentrated as follows. The crystals is recrystallized from methanol solution and the mother liquor is separated from crystals. In this mother liquor, the methyl ester of original pepstatin was almost non-existent and the purified methyl ester of new pepstatins can be recrystallized as fine needle from this mother liquor.

The procedures in this invention includes the methods of obtaining alkaline salts of new pepstatins by alkaline hydrolysis of new pepstatin alcohol esters and the free form of the new pepstatins by neutralization of the above alkaline hydrolysate. The alkaline hydrolysis can be carried out by the same procedure described in the patent application of original pepstatin. (Japanese Patent Application No. 46166/69). The alkaline salts of new pepstatins, thus obtained as sodium salt of pepstatin B is a white amorphous powder having a decomposition point of 250°–255°C and showing 50% inhibition of pepsin ($ID_{50}$) at 0.055 $\gamma$ and $ID_{50}$ was 0.05 $\gamma$. In contrast to pepstatin, pepstatin B (free form) was amorphous form of white powder which was obtained by recrystalization from methanol/$H_2O$ (2:1). It decomposed at about 210°–220°C. Specific rotation, $[\alpha]_D^{20}$ was −85°C (C=1.0, methanol). Its infrared spectrum is shown in FIG. 2. It is easily soluble in methanol (100 mg/ml), 10 times as much as original pepstatin. It is also soluble in aqueous butanol, ethanol, isopropylalcohol, dimethylformamide, dimethylsulfoxide, acetic acid or pyridine and slightly soluble in aqueous acetone, but hardly soluble in dehydrated acetone, dehydrated butanol, chloroform, benzene, ether and water.

The present invention will be explained more in detail by way of examples but is not limited by these examples.

EXAMPLE 1

A strain of Streptomyces testaceus (ATCC No. 21469) producing pepstatin was inoculated in a sterilized medium containing glucose 5.5%, soybean oil 2.0%, skimmed milk 4.5%, milk casein 5.0%, $K_2HPO_4$ 0.15%, NaCl 0.35%, $MgSO_4$ $7H_2O$ 0.15% (pH 6.45) of 2900 l volume and incubated at 23°–24°C for 112 hours with aeration and agitation. The broth contained antipepsin principle equivalent to 2260 $\gamma$/cc of pepstatin. The pH of the broth was adjusted to 2.5 with diluted sulfuric acid and methanol of 3600 l was added. After this liquor was stirred for 40 minutes at 15°–20°C, 4% of filter aid was added and filtered and washed. The methanol eluate of 6300 l thus obtained was adjusted to pH 10 by alkali and evaporated methanol in vacuo to yield aqueous residue of 1900 l. To this aqueous residue, n-butanol of 800 l was added and pH of the mixture was adjusted to 7.0. After agitation for 30 minutes at 20°C, butanol extract of 960 l was separated. The pH of this butanol extract was adjusted to 3.0 and concentrated in vacuo to yield concentrated syrup of 55 l. This syrup was dropped into water of 800 l by drop-wise with stirring for 60 minutes and the precipitates thus formed was filtered. The precipitate was washed with water and lyophilized to obtain yellow colored crude powder of new pepstatins of 7990 g. Anti-pepsin principle equivalent to pepstatin was contained in 64% of the powder.

The crude powder of 6080 g. obtained was dissolved in methanol of 33 l volume and added with active carbon of 1.25 kg to decolorize. To this decolorized methanol solution of 38 l, concentrated sulfuric acid of 125 cc was added and stirred for 2.5 hours at 60°C. The reaction mixture was neutralized by addition of 0.63 l triethylamine and stirred for 120 minutes at 50°–60°C, and obtained white crystalline powder. This powder was washed and dried in vacuo to yield 3230 g. of new pepstatin methyl esters having antipepsin activity ($ID_{50}$) at 0.056 $\gamma$. Its decomposition point was at 250°–251°C and $[\alpha]_D^{20}$ is −90° (C=1.0, acetic acid). This powder contained more than 80% of pepstatin B methyl ester (Rf 0.39 on thin layer chromatography).

EXAMPLE 2

New pepstatin methyl ester of 3100 g. obtained in Example 1 was dissolved in 130 l of 0.2N-NaOH-90% methanol at 60°C to saponify for 2 hours. The reaction mixture was concentrated in vacuo to evaporate methanol and muddy concentrate was obtained. The concentrate was dissolved in 20 l of water saturated n-butanol and added with 15 l of water and adjusted pH to 3.0 by diluted fulfuric acid. After stirring for 20 minutes, upper butanol layer of 18 l was dropped into water of 270 l by drop-wise. The precipitate thus obtained after agitation for 60 minutes was filtered and washed with water. The washed precipitate was dried in vacuo to give white powder of 2500 g. This powder showed decomposition point at 205°–210°C and $[\alpha]_D^{20}$ = −84° (C=1.0, methanol). $ID_{50}$ (50% inhibition against pepsin) was 0.55$\gamma$ Titration curve showed 700 mg of the sample consumed 9.7 cc of 0.1N NaOH.

EXAMPLE 3

100 g. of new pepstatin methyl esters obtained in Example 1 were dissolved in 4 l of absolute methanol and decolorized with 20 g. of active carbon. The methanol solution was kept to stand over night and obtained 24 g. of white crystals at first. 4.2 l of the methanolic mother liquor was concentrated to 1.3 l and precipitation occured. This precipitate was crystalized after 60 minutes with agitation at 60°C. Secondary crystalization over night gave white crystals of 5.5 g. as secondary crop. This second crystals were dissolved in 1.5 l of hot methanol and treated with active carbon. The methanolic solution was kept to stand over night and obtained 12.0 g. of white crystals as third crop.

The above three crystalline substances showed following physico-chemical properties:
The first crystals:
Decomposition point: 250°–251°C $[\alpha]_D^{20} = -90.5°$ (C=0.5, acetic acid)
$ID_{50} = 0.05 \gamma$
Rf 0.35 substance: Rf 0.39 substance =1:1 - 1:2
(thin layer chromatograph, chloroform: methanol : acetic acid = 95:4:1)
The second crystals:
Decomposition point: 253°-254°C
$[\alpha]_D^{20} = -91.5°$ (C=0.5 acetic acid)
$ID_{50} = 0.05 \gamma$.
Mainly Rf 0.35 substance and tract of Rf 0.42 substance
(thin layer chromatograph, chloroform: methanol : acetic acid = 95:4:1)
The third crystals:
Decomposition point: 254°-255°C
$[\alpha]_D^{20} = -95.5°$ (C=0.5, acetic acid)
$ID_{50} = 0.05$
Mainly Rf 0.39 substance (pepstatin B) and trace of Rf 0.42 substance
(thin layer chromatography, chloroform: methanol : acetic acid = 95:4:1)
Infrared spectrum is shown in FIG. 1
Elementary analysis (found); C, 60.14%; H, 9.38%; N, 9.74%.
Moderately soluble in dimethylsulfoxide, demethylformamide and acetic acid, hardly soluble in methanol (5-10 mg/cc) but more soluble than pepstatin methyl ester.

EXAMPLE 4

Pepstatin producing strain (*Streptomyces argenteolus var. toyonakensis* (ATCC No. 21468) was inoculated in a sterilized medium of 130 l containing glucose 6.0%, glycerine 2.0%, skimmed milk 4.0%, milk casein 4.5%, $K_2HPO_4$ 0.1%, NaCl 0.3%, $MgSO_4 \cdot 7H_2O$ 0.1% (pH 6.8) and incubated for 137 hours under the same conditions in Example 1. The cultured broth of 125 l containing anti-pepsin principle equivalent to 170 g. of pepstatin was added with n-butanol of 60 l and stirred for 40 minutes at room temperature. Afterwards, butanol layer, water layer and solid layer (mycelial mass) were separated by centrifugation. The butanol layer was washed with water and concentrated in vacuo to 1.5 l of syrup. pH of the syrup was adjusted to 3.0 and added 7.5 l of n-hexane to yield yellowish brown precipitate with stirring. After stirring for 60 minutes, the precipitate was filtered, washed and dried in vacuo, and yielded 164g. of new crude pepstatin, having anti-pepsin activity of $ID_{50} = 0.075 \gamma$.

150 g. of new pepstatin was dissolved in 1.5 l of 90% methanol at 40°-50°C and decolorized by 150 g. of active carbon. 1.6 l of the decolorized methanol solution was added with 1.0 l of water at room temperature and yielded gel-precipitate. The precipitate was filtered, washed with 50% methanol and lyophilized to give 94 g. of slightly yellowish powder. Its $ID_{50}$ against pepsin was $0.062 \gamma$. This powder was dissolved in 90% of methanol and repeated twice to treat with active carbon as above, and 45 g. of white new pepstatin powder was obtained. Its $ID_{50}$ was $0.055 \gamma$. It showed decomposition point at 198°-205°C and $[\alpha]_D^{20} = -79°$ (C=1.0, methanol). On thin layer chromatograph, it showed Rf 0.35 (pepstatin), Rf 0.39 (pepstatin B and pepstatin C) and Rf 0.42.

EXAMPLE 5

Pepstatin producing strain (*Streptomyces testaceus* ATCC No. 21469) was inoculated in 130 l of a sterilized medium containing glucose 6.0%, glycerine 2.0%, skimmed milk 1.5%, casein 1.5%, soybean meal 5.7%, $K_2HPO_4$ 0.1%, NaCl 0.3% and $MgSO_4 \cdot 7H_2O$ 0.1% (pH 5.5) and incubated for 137 hours under the same conditions in Example 1. To 110 l of the cultured broth containing anti-pepsin principle equivalent to 132 g. of pepstatin was filtered with addition of filter-aid 7 kg and adjusted to pH 2.0 with diluted sulfuric acid, and separated mycelial cake of 33 kg (wet weight) and filtrate of 75 l. Mycelial cake was added with 83 l of absolute methanol to give slurry which was then stirred for 40 minutes. Thereafter, the slurry was filtered and the cake was washed twice with 40 l of 70% methanol to yield 140 l of aqueous methanol eluate. 75 l of the above filtered broth was added with 35 l of N-butanol and stirred for 15 minutes, and separated 37 l of butanol layer from 73 l of water layer. 140 l of above aqueous methanol eluate obtained from mycelial cake was concentrated in vacuo to 27 l of aqueous solution and was mixed with 37 l of above butanol extract obtained from the broth filtrate. This mixture was centrifuged to remove water layer and obtain 35 l of butanol extract. The butanol extract was adjusted to pH 3.0 and concentrated in vacuo to 1.0 l of syrup. This syrup was dropped into 15 l of water by drop-wise and stirred for 60 minutes to yield precipitate. The precipitate was filtered, washed with water and dried at 60°-70°C to give 158 g. of yellowish powder of new pepstatin. Its 50% inhibition against pepsin ($ID_{50}$) was $0.072 \gamma$. The powder thus obtained was esterified in methanol as described in Example 1 to give 62 g. of white crystalline powder of new pepstatin methyl ester. It's $ID_{50} = 0.05 \gamma$, decomposition point 250°-252°C and $[\alpha]_D^{20} = -90.6°$ (C=0.5, acetic acid). On thin layer chromatography, it was found to contain mainly new pepstatin methyl ester (Rf 0.39) and trace of pepstatin methyl ester.

30 g. of this new pepstatin methyl ester thus obtained was saponified in 450 cc of 0.2N-NaOH-90% methanol solution for 2 hours at 60°C. The reaction mixture was adjusted to pH 8.5 with diluted HCl and concentrated to 150 cc forming white precipitate. The precipitate was filtered, washed with methanol and dried in vacuo to yield white powder (17.9 g.) of new pepstatin sodium salt having $ID_{50} = 0.05 \gamma$, decomposition point at 245°-249°C and $[\alpha]_D^{20} = -84°$ (C=1.0, methanol). Its 700 mg consumed 10.1 cc of 0.1N-HCl by titration.

EXAMPLE 6

Pepstatin producing strain (*Streptomyces argenteolus var. toyokensis* ATCC No. 21468) was inoculated in a sterilized medium (130 l) containing glucose 6.0%, glycerine 2.0%, milk casein 4.2%, peptone 1.0%, $K_2HPO_4$ 0.1%, NaCl 0.3% and $MgSO_4 \cdot 7H_2O$ 0.1% (pH 7.0) and incubated for 132.5 hours under the same conditions in Example 1. The cultured broth of 130 l containing anti-pepsil principle equivalent to 111 g. of pepstatin was treated in the same way described in Example 1 and yielded 133 g. of crude new pepstatin, having $ID_{50}$ against pepsin = $0.076 \gamma$.

The yellow powder thus obtained was treated in the same way described in Example 1 and yielded 58.5 g. of new pepstatin methyl ester having $ID_{50} = 0.051 \gamma$, decomposition point at 255°-256°C and $[\alpha]_D^{20} = -95.5°$ (C=0.5, acetic acid). On thin layer chromatograph, it gave Rf 0.35 and Rf 0.39 (1:1) but Rf 0.42 was not observed. When pepstatin preparation thus obtained contained pepstatin equal amount to new pepstatin (1:1).

EXAMPLE 7

Free acid form of new pepstatin (4.0 g.) obtained in Example 2 was dissolved in 100 cc of absolute methanol under heating and added 0.2 cc of conc. $H_2SO_4$. This mixture was refluxed for 6 hours on a boiling water bath and concentrated in vacuo to 50 cc. The precipitate thus formed was filtered, washed with ethanol and dried to give 1.6 g. of powder. The powder was recrystalized from absolute methanol solution (100 cc) and obtained 1.15 g. of white crystalline powder of new pepstatin ethyl ester (pepstatin B ethyl ester), having $ID_{50} = 0.054$ γ, decomposition point at 250°–251°C and $[\alpha]_D^{20} = -90°$ (C=0.5, acetic acid).

EXAMPLE 8

3.0 g. of new pepstatin obtained in Example 2 was dissolved in 100 cc of absolute n-propylalcohol under heating and added 0.2 cc of conc. $H_2SO_4$, and esterified for 6 hours at 80°C. The reaction mixture was concentrated in vacuo to 20.0 cc producing precipitate. The precipitate was filtered, washed with n-propylalcohol and dried to give 900 mg of white powder. This powder was recrystallized from 40.0 cc of absolute propylalcohol solution and 480.0 mg of white powder (pepstatin B n-propylester) was obtained. It showed $ID_{50} = 0.073$ γ, decomposition point at 218°–220°C and $[\alpha]_D^{20} = -89.5°$ (C=0.5, acetic acid).

EXAMPLE 9

3.0 g. of new pepstatin obtained in Example 2 was dissolved in 100 cc of warm absolute n-butanol and added 0.2 cc of conc. $H_2SO_4$. Esterification was made for 6 hours at 80°C and concentrated in vacuo to 2.0 cc containing precipitates. The precipitate was filtered, washed with n-butanol and dried to yield 800.0 mg of white powder. This was recrystallized from 15.0 cc of n-butanol solution and obtained 340 mg of white powder (new pepstatin B n-butyl ester) having $ID_{50} = 0.084$ γ, decomposition point at 205°–207°C and $[\alpha]_D^{20} = -88°$ (C=0.5, acetic acid).

EXAMPLE 10

Pepstanone A was found as a minor active component in the crude pepstatin preparation of Ex. 1. On silica gel thin-layer chromatogram developed with chloroform, methanol, and acetic acid (92.5:6:1.5), pepstanone A gave an Rf value 0.45, while pepstatins gave 0.15 detected by Rydon-Smith reagent. Pepstanone A was isolated by silica gel column chromatography using the same solvent. After crystallization with methanol, fine needles of pepstanone A was obtained. It showed 78 86% of the pepsin-inhibitory activity of pepstatin A.

The new compound melted at 263°–265°C. The molecular formula was established as $C_{33}H_{61}O_7N_5$ (M.W. 639), [Found : C, 61.99; H, 9.81; N, 11.03. Calcd.: C, 61.94; H, 9.61; N, 10.95]. The molecular weight was confirmed by mass spectrometry, [M+, m/e 639]. Pepstanone A gave positive reaction with Rydon-Smith and Brady (2,4-dinitrophenylhydrazine) reagents, but was negative to ninhydrin. Potentiometric titration, electrophoretic behavior, and color reactions suggested that there is no free carboxyl or amino group. The UV [λ$_{max}^{MeOH}$ 280 nm ( ε 114)] and IR [$\nu_{c=o}$ 1715 cm$^{-1}$] absorptions suggested the presence of a keto-group, which accounts for the positive Brady reaction.

Pepstanone A was hydrolyzed with 6 N HCl at 105°C for 15 hours. The amino acid analysis indicated the presence of one mole of alanine, two moles of valine, and one mole of 4-amino-3-hydroxy-6-methylheptanoic acid. The presence of iso-valeric acid was confirmed by gas chromatography of the hydrolyzate after esterification of the acidic ether extract. However, there could not be found a Brady positive substance in the hydrolyzate.

The 2,4-dinitrophenylhydrazone of pepstanone A was obtained as yellow needles, m.p. 268°–270°C. It has still 37% of the activity of pepstatin. The results of the elemental analysis agreed with the formula $C_{39}H_{65}O_{10}N_9$ for the hydrazone. [Found : C, 56.86; H, 8.01; N, 14.63. Calcd. for $C_{39}H_{65}O_{10}N_9$ (M.W. 819): C, 57.13; H, 7.99; N, 15.37]. The UV absorption maximum appeared at 358 nm (ε19,800) in methanol.

Acid hydrolysis of the hydrazone yielded a yellow substance (v), which showed a positive ninhydrin reaction. Compound V was isolated by silica gel column chromatography using chloroform and methanol (9:1) and was crystallized with mixed solvent of ethyl acetate and methanol, m.p. 202°–206°C, $\lambda_{max}^{MeOH}$ 350nm (ε 18,300). The molecular formula was established as $C_{13}H_{19}O_4N_5.2$ HCl, [Found: C, 41.26; H, 5.30; N, 18.34; Cl, 18.37. Calcd: C, 40.85; H, 5.54; N, 18.32; Cl, 18.55]. The mass spectrum showed the parent peak at m/e 309 ($C_{13}H_{19}O_4N_5$) and the base peak at m/e 252 (M-$C_4H_9$). The NMR spectrum was taken in DMSO-d$_6$ solution as internal TMS reference [0.98 (δ) (3H, doublet, J=5.5 Hz), 1.00 (3H, doublet, J=5.5 Hz), 1.6 1.8 (3H, multiplet), 2.21 (3H, singlet), 4.18 (1H, triplet, J=6.5 Hz), 8.2 9.1 (3H, aromatic H), 8 9.5 (broad NH)].

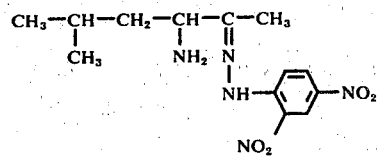

v

From the above results structure V was deduced. Then the C-terminus of pepstanone A was suggested to be 3-amino-5-methylhexanone-2. The amino acid sequence in pepstanone A was expected to be the same as that of pepstatins. The mass spectra of pepstanone A and the O-trimethylsilyl derivative (FIG. 1) unambiguously supported the sequence.

We claim:

1. A compound having the formula:

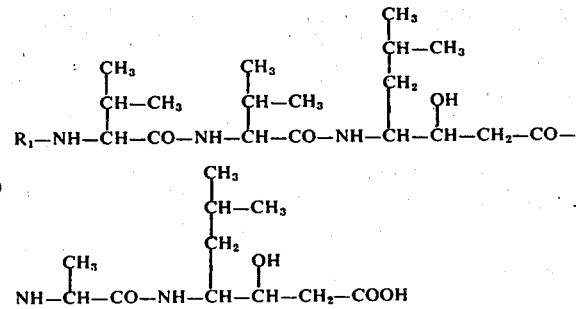

wherein $R_1$ is n-caproyl or an alkyl ester thereof wherein the alkyl group contains 1–4 carbon atoms.

* * * * *